US012104136B2

(12) United States Patent
Moran et al.

(10) Patent No.: US 12,104,136 B2
(45) Date of Patent: Oct. 1, 2024

(54) LUBRICIOUS AND DURABLE COATINGS FOR MEDICAL APPLIANCES

(71) Applicant: Merit Medical Ireland Limited, Galway (IE)

(72) Inventors: Martin Moran, Galway (IE); Emmanouil Kasotakis, Galway (IE)

(73) Assignee: Merit Medical Ireland Limited, Galway (IE)

( * ) Notice: Subject to any disclaimer, the term of this patent is extended or adjusted under 35 U.S.C. 154(b) by 0 days.

(21) Appl. No.: 17/326,041

(22) Filed: May 20, 2021

(65) Prior Publication Data

US 2021/0363452 A1    Nov. 25, 2021

Related U.S. Application Data

(60) Provisional application No. 63/029,209, filed on May 22, 2020.

(51) Int. Cl.
| | |
|---|---|
| *C10M 107/44* | (2006.01) |
| *A61L 29/08* | (2006.01) |
| *A61M 25/00* | (2006.01) |
| *C10M 107/28* | (2006.01) |
| *C10N 40/00* | (2006.01) |
| *C10N 50/00* | (2006.01) |

(52) U.S. Cl.
CPC ......... *C10M 107/44* (2013.01); *A61L 29/085* (2013.01); *A61M 25/0045* (2013.01); *C10M 107/28* (2013.01); *A61L 2400/10* (2013.01); *A61L 2420/02* (2013.01); *A61L 2420/06* (2013.01); *A61L 2420/08* (2013.01); *A61M 2025/0046* (2013.01); *C10M 2209/0845* (2013.01); *C10M 2209/0863* (2013.01); *C10M 2217/0453* (2013.01); *C10N 2040/50* (2020.05); *C10N 2050/023* (2020.05)

(58) Field of Classification Search
CPC ............... A61L 29/085; A61L 2400/10; A61L 2420/02; A61L 2420/06; A61L 2420/08; A61M 25/0045; A61M 2025/0046; C10M 107/28; C10M 107/44; C10M 2209/0845; C10M 2209/0863; C10M 2217/0453; C10N 2040/50; C10N 2050/023
See application file for complete search history.

(56) References Cited

U.S. PATENT DOCUMENTS

| 4,666,819 | A | * | 5/1987 | Elmasry | .................. C09B 69/10 |
| 5,891,109 | A | | 4/1999 | Inoue et al. | |

(Continued)

FOREIGN PATENT DOCUMENTS

CN    105985720    10/2016

OTHER PUBLICATIONS

International Search Report and Written Opinion dated Aug. 31, 2021 for PCT/EP2021/1063586.

(Continued)

*Primary Examiner* — James C Goloboy
(74) *Attorney, Agent, or Firm* — Dorsey & Whitney LLP (57) ABSTRACT

Coatings for medical devices having selectable levels of durability and lubricity are disclosed. The coatings include polymeric material components, the characteristics and relative amounts of which can be selected to provide target levels of durability and lubricity. Methods of making the coatings for medical devices are also disclosed.

15 Claims, 4 Drawing Sheets

(56) References Cited

U.S. PATENT DOCUMENTS

| | | | |
|---|---|---|---|
| 10,376,614 B2 | 8/2019 | Kohama et al. | |
| 2007/0270515 A1* | 11/2007 | Chmielewski | C08F 283/045 |
| | | | 520/1 |
| 2008/0091168 A1 | 4/2008 | Ameno et al. | |
| 2008/0102378 A1* | 5/2008 | Cole | G11B 7/253 |
| | | | 430/2 |
| 2010/0273096 A1* | 10/2010 | Askham | G03F 7/027 |
| | | | 430/2 |
| 2011/0200828 A1* | 8/2011 | Li | A61L 27/34 |
| | | | 428/522 |
| 2016/0175492 A1* | 6/2016 | Kohama | A61L 29/14 |
| | | | 427/2.24 |

OTHER PUBLICATIONS

International Search Report and Written Opinion dated Nov. 17, 2022 for PCT/EP2021/063586.

* cited by examiner

LUBRICIOUS AND DURABLE COATINGS FOR MEDICAL APPLIANCES

CROSS-REFERENCE TO RELATED APPLICATIONS

This application claims priority to U.S. Provisional Application No. 63/029,209, filed May 22, 2020, and titled LUBRICIOUS AND DURABLE COATINGS FOR MEDICAL APPLIANCES, which is hereby incorporated by reference in its entirety.

TECHNICAL FIELD

The present disclosure relates generally to coatings for medical appliances. More specifically, the present disclosure relates to polymeric coatings for medical appliances, the polymeric coatings having high levels of durability and selectable lubricity. Related methods are also disclosed.

BRIEF DESCRIPTION OF THE DRAWINGS

The embodiments disclosed herein will become more fully apparent from the following description and appended claims, taken in conjunction with the accompanying drawings. These drawings depict only typical embodiments, which will be described with additional specificity and detail through use of the accompanying drawings in which:

DETAILED DESCRIPTION

The components of the embodiments as generally described and illustrated herein can be arranged and designed in a wide variety of different configurations. Thus, the following more detailed description of various embodiments is not intended to limit the scope of the present disclosure, but is merely representative of various embodiments. It will be appreciated that various features are sometimes grouped together in a single embodiment, figure, or description thereof for the purpose of streamlining the disclosure. Many of these features may be used alone and/or in combination with one another.

Medical devices or appliances, such as catheters, guidewires, hypotubes, stylets, etc., can be inserted into a patient for diagnostic or therapeutic procedures. In accordance with the present disclosure, a coating may be used for such an elongated medical device (e.g., a catheter, guidewire, hypotube, stylet, etc.). For example, the coating may be applied to or disposed on at least a portion of a surface of the medical device. The coating may comprise one or more biocompatible polymeric materials, where each polymeric material or the particular combination thereof is selected to impart particular properties to the coating. For instance, with regard to medical devices such as catheters, guidewires, stylets and the like, lubricity and durability can be of particular relevance to typical use of these devices, which can involve navigating tortuous but delicate anatomical features to reach a target site while effectively transiting intervening areas of resistance.

The terms "lubricious" and "lubricity," as used herein, refer to the characteristic of being smooth or slippery, or of possessing a low coefficient of friction. Higher levels of lubricity can correspond to lower coefficients of friction, and lower levels of lubricity can correspond to higher coefficients of friction. As further detailed below, the lubricity of a coating can also be related to the hydrophilicity of the coating.

The term "durability" refers to the coating's ability to withstand wear or degradation. Increased durability may render a medical appliance less susceptible to wear during, or as a result of, use in a medical procedure. For example, increased durability allows the medical appliance to withstand change in a significant and/or detrimental way during a medical procedure. Increased durability may also decrease the extent to which the coating (or an outermost layer of the coating) is removed (e.g., by being dissolved in an aqueous or biological environment).

As further detailed below, in some embodiments a coating for a medical device comprises a base coating layer and a top coating layer, where the top coating layer comprises two or more polymeric components. The types and relative amounts of the components of the top coating layer can be selected to impart particular levels of lubricity and durability to the coating.

The base coating layer can be the coating layer disposed nearest to an exterior surface of the medical device. In some embodiments, the base coating layer is in direct contact with the exterior surface of the device. In other embodiments, one or more additional base or primer layers can be disposed on the exterior surface of the device, upon which the base coating layer can thereafter be applied. In certain embodiments, the polymeric material for the base coating layer can be selected to bind or adhere to the medical device surface and to provide a sufficient foundation for the coating.

In a particular embodiment, the polymeric material of the base coating layer can be selected for a particular physical property, such as toughness. In certain embodiments, the polymeric material has a Shore hardness of from about 80 A to about 99 A, and more particularly from about 90 A to about 95 A. In some embodiments, the base coating layer comprises a polyurethane. The polyurethane can be a copolymer, such as an alternating copolymer or a block copolymer. In certain embodiments, the polyurethane is a block copolymer comprising at least two types of monomers. In such polyurethanes, a block of a particular type of monomer or a particular combination of monomers exhibits certain physical properties, and the arrangement and relative abundance of various blocks can determine the physical properties of the copolymer. In some embodiments, the polyurethane includes blocks having both hard or rigid segments as well as softer, more elastic segments. For example, a block can include hard segments comprising a number of urethane linkages in combination with soft segments comprising a number of aliphatic monomers joined by ether linkages. Particular levels of hardness or elasticity can be obtained by selecting the molar ratio of these segments. In particular embodiments, the polyurethane of the base coating layer is an aliphatic polyether-based polyurethane. Other aliphatic polyurethanes or aromatic polyurethanes can also be used.

In a particular embodiment, the base coating layer comprises a urethane having the structure of Formula 1:

wherein HMDI is 4,4'-dicyclohexylmethane diisocyanate, PTMEG is polytetramethylene ether glycol, and BD is 1,4-butanediol. In some embodiments, n, p, and q are integers greater than or equal to 1.

In some embodiments, the base coating layer comprises a urethane represented by Scheme 1:

wherein R can include various aromatic or aliphatic groups. For instance, in certain embodiments, the R can include groups to form methylene diphenyl diisocyanate (MDI), toluene diisocyanate (TDI), hexamethylene diisocyanate (HDI), isophorone diisocyanate (IPDI), or 4,4'-dicyclohexylmethane diisocyanate (HMDI, etc. Other R groups can also be used.

As will be appreciated by those of skill in the art with the aid of the present disclosure, other polymeric materials may also be suitable for inclusion in the base coating layer. In particular, materials that are well suited for coating surfaces found in medical devices, including medical grade metals and metal alloys. In particular embodiments, materials in the base coating layer are suited for application to nitinol or nitinol that is optionally jacketed with tungsten-impregnated polyurethane.

In a particular embodiment, the base coating layer has a thickness of from about 2 μm to about 20 μm, and more particularly from about 2 μm to about 10 μm, from about 10 μm to about 20 μm, or from about 5 μm to about 15 μm. However, in accordance with the present disclosure, the thickness of the base coating layer can be selected so as to be suitable for the dimensions of the medical device coated with the coating. For example, in coatings for guidewires, a thicker coating may be used for a larger diameter guidewire than for a guidewire having a thinner diameter.

The coating further comprises a top coating layer disposed on the base coating layer. In other embodiments, the top coating is disposed directly on the medical device (e.g., in instances where the medical device is formed of a polymer such as a polyurethane.) The top coating layer can be an outer or external most layer of the coating and can thereby provide properties with respect to interactions with a working environment of the coated surface of the medical device, such as other medical device surfaces or a body cavity of a subject. In various embodiments, the top coating layer is designed to provide biocompatibility and a particular combination of durability and lubricity. In some embodiments, the top coating layer comprises two or more components among which include polymeric materials selected to make a particular contribution to the durability and/or lubricity of the coating. In particular embodiments, the components include a toughening polymer to provide durability, and a lubricative polymer to impart lubricity.

The toughening polymer can be a polymer or co-polymer selected to provide structural strength and integrity to the top coating layer. In some embodiments, the toughening polymer is selected from: (poly(benzyl methacrylate), poly(butyl methacrylate), poly(tert-butyl methacrylate), poly(cyclohexyl methacrylate), poly(ethyl methacrylate), poly(tetrahydrofurfuryl methacrylate) and poly(methyl methacrylate). In some embodiments, the toughening polymer is an acrylate polymer, i.e., comprising polymerized monomers including acrylate or methacrylate monomers, each of which may be alkylated or unalkylated. In more specific embodiments, the acrylate polymer is a poly(methacrylate), i.e., comprising polymerized unalkylated or alkylated methacrylate monomers. In a particular embodiment, the poly(methacrylate) is a poly(methyl methacrylate), i.e., comprising a polymerized monomer having the structure:

Formula 2

In certain embodiments, x is between about 20 and about 30,000. In additional embodiments, the poly(methyl methacrylate) has a molecular weight of between about 2,000 and about 3,000,000 g/mol.

Poly(methyl methacrylate), also referred to hereinafter as PMMA, used in accordance with the described embodiments can be a homopolymer or alternatively modified with other comonomers such as acrylates and alkyl acrylates. Other modifications that may be suitable for use in this application are also contemplated by the present disclosure, as will be recognized by those of skill in the art with the aid of said disclosure.

As mentioned above, the lubricity of the coating can be related to the hydrophilicity of the coating as a whole, or more particularly the top coating layer, or still more particularly to the hydrophilicity of one or more polymer components of top coating layer. In some embodiments, at least one component of the top coating layer is a lubricative polymer that is hydrophilic or capable of being rendered hydrophilic to some degree, where the lubricity of the coating is at least in part a product of the level of hydrophilicity of said lubricative polymer. In particular embodiments, the lubricative polymer is a polymer or copolymer in which at least one of the constituent monomers is a salt monomer, i.e., the monomer includes an acidic or basic moiety that is associated with a counterion to form a salt. In particular embodiments, the salt monomer is a monovalent salt, i.e., having a counterion such as $Na^+$, $K^+$, $Li^+$. In one embodiment, the salt monomer is a sodium salt. In other embodiments, the salt monomer is a divalent salt, i.e., having a counterion such as $Mg^{++}$ or $Ca^{++}$.

In some embodiments, a salt monomer in the lubricative polymer arises from a saltable monomer, i.e., a monomer that is nonionic until subjected to an activation reaction that converts certain functional groups into acidic or basic groups. In some of these embodiments, the saltable monomer is an acid anhydride that can be converted to an acid upon activation. In some embodiments, the lubricative polymer comprises maleic acid or a salt thereof. In more particular embodiments, the lubricative polymer is a maleic anhydride polymer in which at least a portion or all of the maleic anhydride monomers are converted to maleic acid monomers and maleic acid salt monomers. In a particular embodiment, the maleic anhydride polymer is a poly(methyl vinyl ether-co-maleic anhydride) as in Formula 3 in which anhydride monomers are converted in the activated coating to maleic acid (Formula 4) and maleic acid sodium salt (Formula 5). In particular embodiments, all of the anhydride monomers are converted into maleic acid sodium salt (Formula 5):

Formula 3

In certain embodiments, n is between about 840 and about 12,900. In additional embodiments, the molecular weight is between about 130,000 and about 3,000,000 g/mol.

Formula 4

Formula 5

In some embodiments, the maleic acid salt monomers are optionally converted to divalent salts as in Formulas 6 and 7:

The inclusion of a plurality of components in the top coating layer provides for coatings having selected levels of certain properties by selecting the ratio of amounts of the components. In particular, various ratios of lubricative polymer to toughening polymer included in the top coating layer of the coatings described herein can provide coatings having different levels of lubricity and durability. Accordingly, in some embodiments, the weight ratio of the toughening polymer to the lubricative polymer in the top coating layer is between about 0.001:100 and about 4:100, or between about 0.1:100 to about 2:100. Other ratios can also be used.

In an aspect, the weight fractions of lubricative polymer and toughening polymer in the top coating layer can be selected by incorporating polymer chains of each of having chain lengths or molecular weights within selected ranges. For example, in some embodiments, the molecular weight of the toughening polymer (e.g., PMMA) is between about 2,000 and about 3,000,000 g/mol, between about 50,000 and about 1,000,000 g/mol, or between about 50,000 and about 500,000 g/mol. In certain embodiments, the molecular weight of the lubricative polymer is between about 130,000 and about 3,000,000 g/mol, or between about 1,250,000 and about 2,500,000 g/mol. Other molecular weights can also be used.

While not wishing to be bound to a particular theory, it is contemplated that the components of the top coating layer can exhibit an arrangement within that layer that also contributes to the physical and chemical properties of the coating. In some embodiments, the component polymers form one or more polymer chain networks within the top coating layer. In some embodiments, only certain components of the top coating layer are chemically bound or otherwise directly adhered to the underlying base coating layer. In such embodiments, other components can form a network that is interpenetrating or semi-interpenetrating with the polymers attached to the base coating layer. In certain embodiments, the lubricative polymer is bound to the base coating layer.

Figure 1:
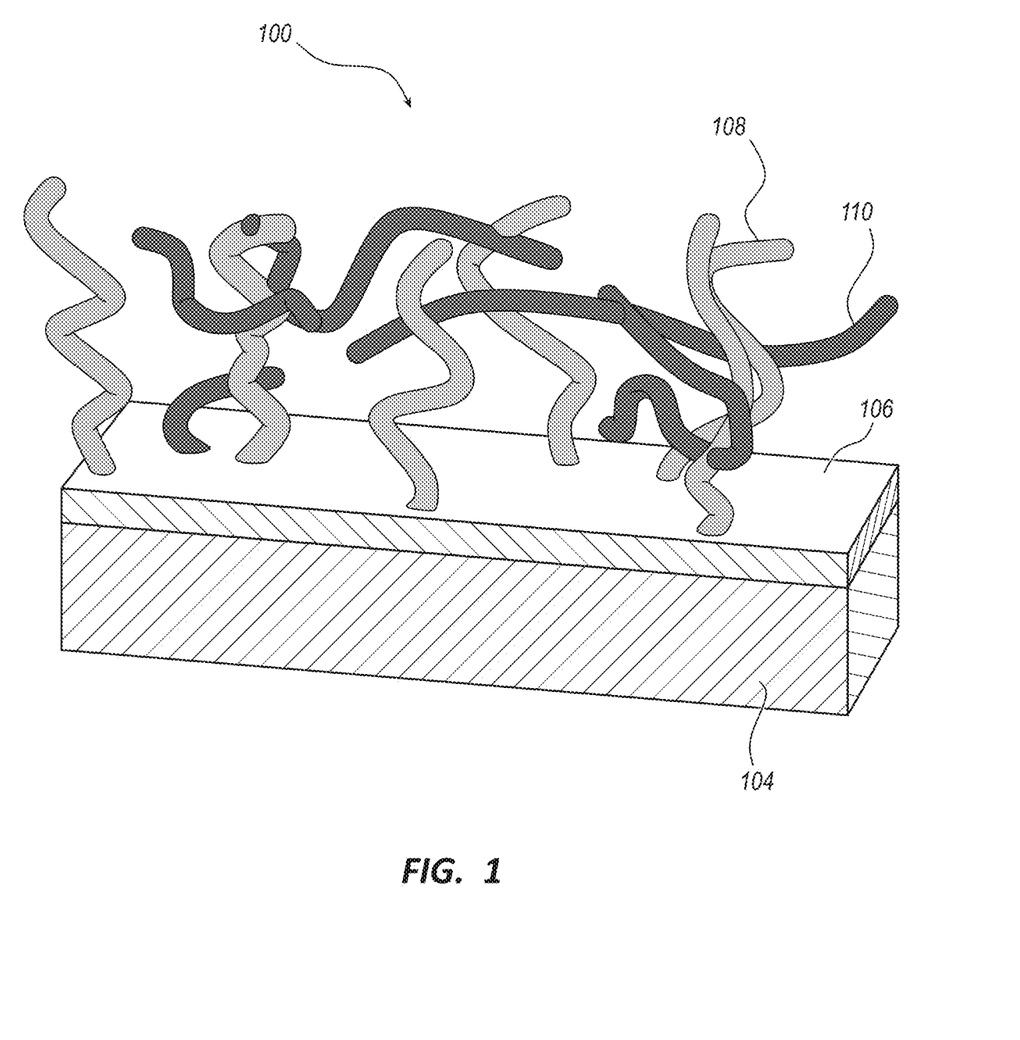
FIG. 1 depicts a representation of the structure of a coating in accordance with an embodiment.

FIG. 1 shows a representation of the various polymer components in an illustrative embodiment of a coating 100 comprising PMMA as the toughening polymer 110 and a poly(methyl vinyl ether-co-maleic anhydride) as the lubricative polymer 108. As shown in FIG. 1, the lubricative polymer chains 108 are chemically bound to the underlying polyurethane base coating layer 106, which is disposed on a polyurethane-tungsten jacket 104 of a medical device, while the PMMA polymer chains 110 form a semi-interpenetrating polymer network with the poly(methyl vinyl ether-co-maleic anhydride) 108.

In some embodiments, the top coating layer can optionally further comprise a crosslinker. It will be recognized by those of skill in the art with the aid of the present disclosure that a number of approaches and agents may be suitably employed to provide crosslinking in polymeric material. Available crosslinkers that establish crosslinking under a wide variety of stimuli including but not limited to, light, pH, temperature, hydration, and various chemical agents. In certain embodiments, the crosslinker can form links between crosslinkable moieties in one or more of the component polymers in the top coating layer. In particular embodiments, the crosslinker forms links between crosslinkable moieties in the lubricative polymer, such that the lubricative polymer is at least partially crosslinked. In some embodiments, the crosslinker is an alkoxylated polyol. In particular embodiments, the crosslinker is trimethylolpropane ethoxylate. Other crosslinkers can also be used.

In particular embodiments, the crosslinker is selected to form links with functional groups other than those that contribute to the hydrophilicity of the coating. By way of example, where the lubricative polymer is a copolymer of maleic acid or maleic anhydride with other monomer types, a crosslinker may be used that forms crosslinks with moieties in the other monomers, leaving any maleic acid carboxylate groups free to form salts.

In a particular embodiment, the top coating layer has a thickness of from about 1 µm to about 15 µm, and more particularly from about 1 µm to about 5 µm, from about 5 µm to about 15 µm, or from about 2 µm to about 10 µm. However, in accordance with the present disclosure the thickness of the base coating layer can be selected so as to be suitable for the dimensions of the medical device that is coated with the coating.

Figure 2A:
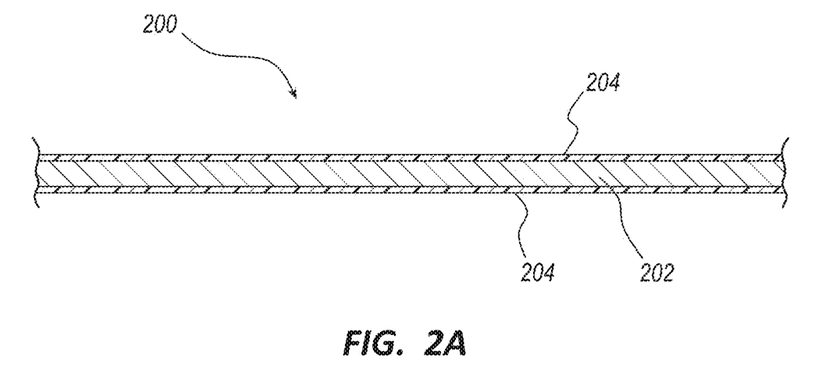
FIG. 2A is a cross-sectional view of a medical device before the application of a layer of a coating.
Figure 2B:
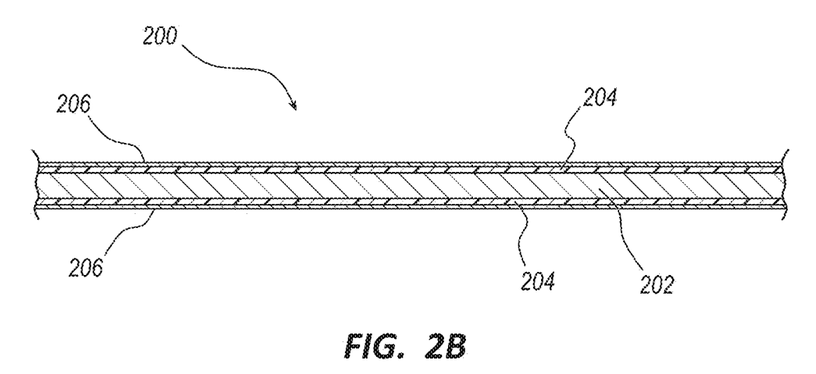
FIG. 2B is a cross-sectional view of a medical device after the application of a base layer of the coating.
Figure 2C:
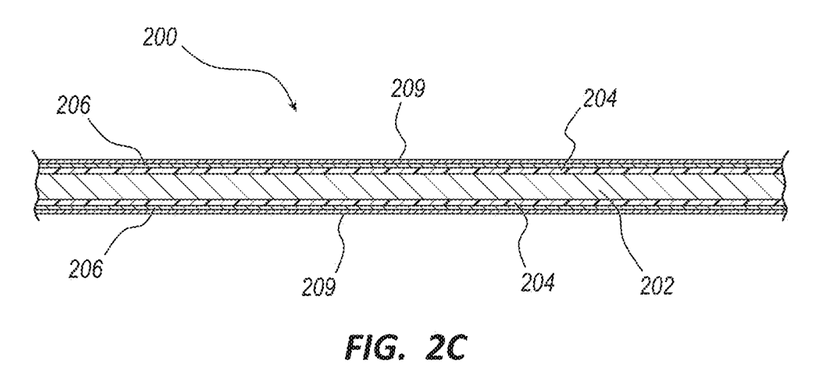
FIG. 2C is a cross-sectional view of a medical device after the application of a top layer of the coating.

In accordance with certain embodiments, a medical device is coated with a durable lubricious coating as described above. FIGS. 2A-2C show cross-sectional views of a guidewire, which is one an example of a medical device 200 that can be coated as disclosed herein. As shown in FIG. 2A, the medical device 200 comprises an elongate body 202 having an exterior surface on or over which the coating is disposed. In some embodiments, the medical device is jacketed, i.e., at least a portion of the exterior surface is covered with a jacket coating 204. Certain medical devices 200, particularly catheters, guidewires and the like, are manufactured with jacket coating 204 designed to provide a measure of hydrophilicity. In cases where the jacket coating material is largely radiotransparent, the jacket coating 204 may be impregnated with materials such as tungsten or barium to confer a level of radiopacity, which aids the use of real-time imaging to guide placement of the device in a subject's body. In some embodiments, the medical device 200 has a jacket coating 204 comprising polyurethane. In some embodiments, the jacket coating 204 comprises polyurethane impregnated with a radiopaque material, such as tungsten.

In certain embodiments, a method of coating a medical device 200 comprises forming a base coating layer 206 comprising a polyurethane on an exterior surface of a medical device body 200 (or on an exterior surface of the jacket coating 204) as illustrated in FIG. 2B. As illustrated in FIG. 2C, a top coating layer 209 can also be formed on the top of the base coating layer 206. As discussed above, the top coating layer 209 can comprise a toughening polymer and a lubricative polymer, where said lubricative polymer comprises a saltable monomer. The top coating layer 209 can also be cured to bind the lubricative polymer to the base coating layer 206; and activated to render the top coating layer 209 hydrophilic.

In some embodiments, forming the base coating layer on the medical device surface involves applying a base coating layer formulation to the surface, where the base coating layer formulation comprises the polymeric materials to be included in the base coating layer and an appropriate solvent. The solvent can be selected based on its ability to solubilize the polymeric material, as well as its suitability for the coating process to be used. In some embodiments, forming the base coating layer includes using a base coating layer formulation comprising a polyurethane and a solvent to coat the medical device surface via a solvent coating method, where the surface is passed through the base coating layer formulation, and then dried to substantially remove the solvent. Solvents appropriate for creating a polyurethane base coating layer by this method include polar solvents having sufficient solvent activity with polyurethane as well as a sufficiently low boiling point that allows effective solvent removal by drying. Particular solvents that may be used include N—N dimethylacetamide (DMA), dimethylformamide (DMF), m-cresol, dimethylsulfoxide (DMSO), methyl ethyl ketone (MEK), toluene, and tetrahydrofuran (THF). In a particular embodiment, the solvent is tetrahydrofuran.

In some embodiments, drying comprises heating the solution on the surface at a temperature and for a time to achieve substantial removal of the solvent. It will be understood that an effective temperature will depend on the boiling point of the solvent used. In some embodiments, the drying temperature is from about 50° C. to about 250° C., and more particularly from about 60° C. to about 100° C., from about 100° C. to about 220° C., from about 80° C. to about 150° C., from about 50° C. to about 90° C., or from about 65° C. to about 75° C. In some embodiments the drying time is from about 15 minutes to about 75 minutes, or more particularly from about 15 minutes to about 40 minutes, from about 30 minutes to about 75 minutes, or from about 20 minutes to about 40 minutes. In an embodiment, drying is done at a temperature of about 60° C. to about 100° C. for about 20 minutes to about 40 minutes.

In some embodiments, forming the top coating layer comprises passing the medical device body including the base coating layer through a top coating layer formulation, where the top coating layer formulation comprises a toughening polymer, a lubricative polymer, and at least one solvent. The toughening polymer included in the top coating layer formulation can be a polymer or co-polymer selected to provide structural strength and integrity to the top coating layer. In some embodiments, the toughening polymer is an acrylate polymer, i.e., comprising polymerized monomers including acrylate or methacrylate monomers, each of which may be alkylated or unalkylated. In more specific embodiments, the acrylate polymer is a poly(methacrylate), i.e., comprising polymerized unalkylated or alkylated methacrylate monomers. In a particular embodiment, the poly(methacrylate) is PMMA. The lubricative polymer in the top coating layer formulation includes at least one saltable monomer. In some of these embodiments, the saltable monomer is an acid anhydride that can be converted to an acid upon activation. In particular embodiments, the lubricative polymer comprises maleic acid or a salt thereof. In more particular embodiments, the lubricative polymer is a maleic anhydride polymer in which at least a portion of the maleic anhydride monomers are converted to maleic acid monomers and maleic acid salt monomers, or all of the maleic anhydride monomers are converted to maleic acid salt monomers. In a particular embodiment, the maleic anhydride polymer is a poly(methyl vinyl ether-co-maleic anhydride).

In some embodiments of the methods herein, the composition of the top coating layer formulation is selected to provide a top coating layer having particular levels of certain properties, particularly lubricity and durability. The top coating layer formulation can optionally comprise a cross-linker.

The top coating layer formulation further includes one or more solvents. The solvent can be selected based on its ability to solubilize the polymeric materials, as well as its suitability for the coating process to be used. In some embodiments, a combination of solvents may be used due to the respective characteristics of the plurality of polymer components in the top coating layer formulation. Particular solvents that may be used include various alkyl ketone and alkyl acetate solvents, such as methyl acetate, methyl ethyl acetate, methyl n-propyl ketone, methyl ethyl ketone, tetrahydrofuran, 1,4-dioxane, ethyl acetate, acetone, cyclohexanone, N-methyl-2-pyrrolidone, dimethyl formamide, dimethyl sulfoxide and the like, and combinations thereof. In some embodiments, the solvent comprises methyl ethyl ketone, methyl acetate, or both.

The method further comprises curing the top coating layer formulation to form the top coating layer. In some embodiments, the curing step is performed to cause binding of one or more polymer components to the base coating layer. In particular embodiments, curing results in binding of the lubricative polymer to the base coating layer. In such embodiments, the curing step comprises heating the top coating layer formulation on the base coating layer for a time and at a temperature to achieve these endpoints. While not wishing to be bound to a particular theory, such a curing step at elevated temperatures promotes the breakdown of hydrogen bonds in the polyurethane of the base coating layer, which facilitates a reaction between the polyurethane and particular monomers in the lubricative polymer. For example, in the case of a lubricative polymer comprising maleic anhydride monomers, the curing step facilitates a thermal reaction of the maleic anhydride with the polyurethane in the base coating layer. In some embodiments where the top coating layer formulation includes a crosslinker, the curing step can be performed so as to achieve crosslinking in at least part of the lubricative polymer chains. In some embodiments, the curing step comprises heating the top coating layer formulation at a temperature of from about 80° C. to about 130° C. for a time of from about 2 hours to about 16 hours, or more particularly at a temperature of from about 100° C. to about 120° C. for a time of from about 3 hours to about 8 hours.

The method further comprises the step of activating the top coating layer. In some embodiments, activating the top coating layer renders the top coating layer hydrophilic. In some embodiments, the activating step involves one or more chemical reactions resulting in the conversion of one or more saltable monomers in the lubricative polymer to salt monomers. In certain embodiments, for example where the saltable monomer is an acid anhydride, activation can progress through two stages: the conversion of anhydride monomers to acid monomers, and the subsequent conversion of the acid monomers to salt monomers. In particular embodiments, the activation step is performed by contacting the coating on the medical device surface with an activating solution composed to convert saltable monomers to a state that increases the hydrophilicity of the lubricative polymer. In some embodiments, an activating solution to convert acid anhydride monomers to salt monomers includes a base, and optionally an alcohol. The activating solution has a pH of from about 9 and about 14. In an example embodiment, an activating solution to convert acid anhydride monomers to sodium salt monomers includes sodium hydroxide, ethanol, and water. In various embodiments, activation is performed by dipping, spraying, rinsing or other suitable means of contacting the coating with the activating solution. In a particular embodiment, the coating is dipped in the activating solution for from about 1 minute to about 30 minutes, or more particularly from about 1 minute to about 10 minutes, or from about 3 minutes to about 15 minutes, or from about 10 minutes to about 30 minutes, or from about 2 minutes to about 5 minutes.

In some embodiments, an optional further step comprises finishing the activated coating to convert salt monomers in the lubricative polymer to divalent salt monomers. In an aspect this step can involve substantially replacing monovalent counterions (e.g., $Na^+$) of acid salt monomers with divalent counterions. In some embodiments, the divalent counterions are $Mg^{++}$, $Ca^{++}$, or both. While not wishing to be bound to a particular theory, it is contemplated that increased stability of divalent salt monomers may provide a more robust coating for storage and for certain uses.

EXAMPLES

To further illustrate these embodiments, the following examples are provided. These examples are not intended to limit the scope of the claimed invention, which should be determined solely on the basis of the attached claims.

Example 1

The lubricity of various coatings was tested by varying the ratio of a toughening polymer (PMMA) to a lubricative polymer (poly(methyl vinyl ether-co-maleic anhydride)) in the top coating layer of a medical device. In doing so, six polyurethane-tungsten jacketed nitinol wires were first coated with a base layer comprising an aliphatic polyether-based polyurethane (2.5% w/v in THF). After the base layer was dried, different top coatings were applied to the six wires, after which the coated wires were each subjected to the same activation step (as set forth herein) to convert the maleic anhydride portion of the lubricative polymer to a maleic acid sodium salt.

The following top coatings were applied to the wires (wherein the amounts are weight ratios):

| Top Coating (Sample #) | Toughening Polymer PMMA (MW 350,000 g/mol) (g) | Lubricative Polymer Poly(Methyl Vinyl Ether-co-Maleic Anhydride) (in Methyl Acetate/Methyl Ethyl Ketone) (g) | Crosslinker (Optional) Trimethylolpropane Ethoxylate (g) |
|---|---|---|---|
| A | 0 | 100 | 0.05 |
| B | 0.25 | 100 | 0.05 |
| C | 0.5 | 100 | 0.05 |
| D | 1 | 100 | 0.05 |
| E | 1.5 | 100 | 0.05 |
| F | 2 | 100 | 0.05 |

Figure 3:
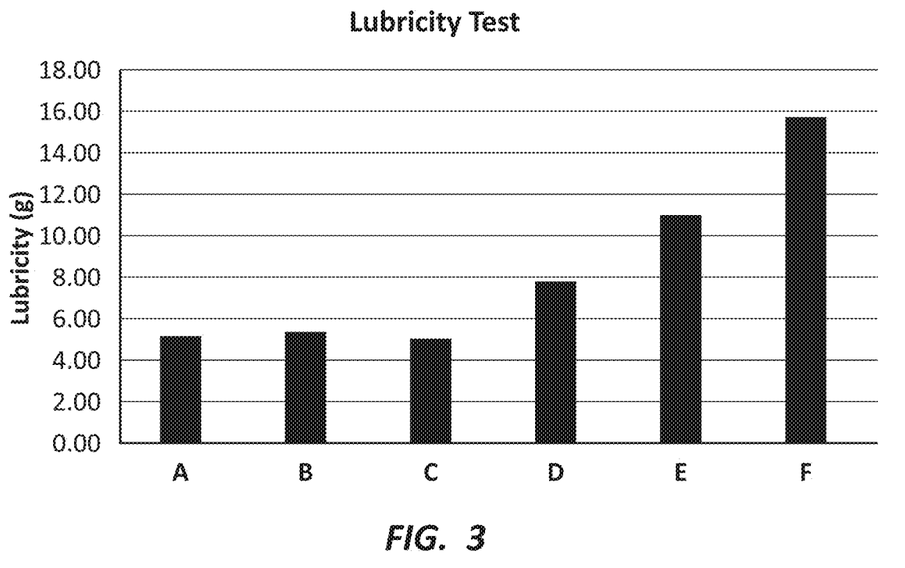
FIG. 3 is a graph of a lubricity test of exemplary coatings.

The lubricity was then measured using an OakRiver Technology DL1000 lubricity/wear tester, and the results are shown in FIG. 3. In the lubricity test, pads were covered with rubber materials, and the test parameters were as follows: test distance (100 mm); cycles (30); speed (10 mm/s); acceleration (200 mm/s); grip force (500 g); environment (PBS 1×, 37° C.). As shown in FIG. 3, the lubricity increased with the addition of PMMA to the top coating formulation.

Example 2

The samples of Example 1 were also subjected to a wear/durability test using an OakRiver Technology DL1000 lubricity/wear tester. In doing so, the pads of the tester were covered with woven gauze before the wire was tested. Initially high grip force was applied and then the wire was pulled with a specific speed. The parameters of the test were as follows: test distance (100 mm); cycles (60); speed (10 mm/s); acceleration (200 mm/s) grip force (900 g); environment (PBS 1×, 37° C.). The results of the wear/durability are depicted in FIG. 4.

Figure 4:
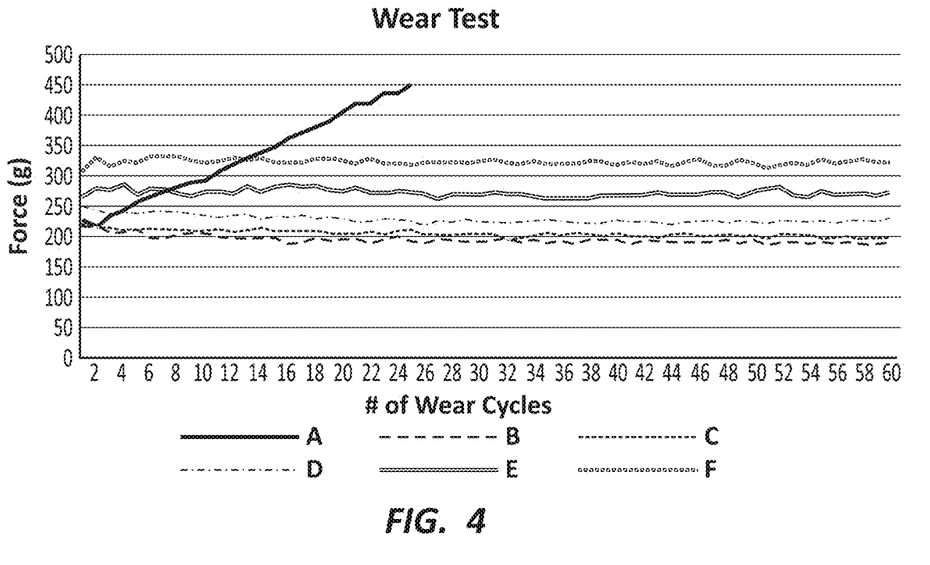
FIG. 4 is a graph of a wear/durability test of exemplary coatings.

As shown in FIG. 4, the lubricity increased with the addition of PMMA to the top coating formulation. The durability was also relatively constant for the samples that contained PMMA (e.g., Samples B-F), as the durability can be represented by the recorded force throughout the 60 cycles.

Example 3

The wear/durability of various coatings was also tested by varying the molecular weight of the toughening polymer (PMMA) in the top coating layer of a medical device. In doing so, two polyurethane-tungsten jacketed nitinol wires were first coated with a base layer comprising an aliphatic polyether-based polyurethane (2.5% w/v in THF). After the base layer was dried, different top coatings were applied to the two wires, after which the coated wires were each subjected to the same activation step (as set forth herein) to convert the maleic anhydride portion of the lubricative polymer to a maleic acid sodium salt.

The following top coatings were applied to the wires (wherein the amounts are weight ratios):

| Top Coating (Sample #) | Toughening Polymer PMMA | Lubricative Polymer Poly(Methyl Vinyl Ether-co-Maleic Anhydride) (in Methyl Acetate/Methyl Ethyl Ketone) | Crosslinker (Optional) Trimethylolpropane Ethoxylate |
|---|---|---|---|
| G | 1 (MW 120,000 g/mol) | 100 | 0.05 |
| H | 1 (MW 350,000 g/mol) | 100 | 0.05 |

Samples G and H were then subjected to a wear/durability test using an OakRiver Technology DL1000 lubricity/wear tester. In doing so, the pads of the tester were covered with woven gauze before the wire was tested. Initially high grip force was applied and then the wire was pulled with a specific speed. The parameters of the test were as follows: test distance (100 mm); cycles (60); speed (10 mm/s); acceleration (200 mm/s) grip force (900 g); environment (PBS 1×, 37° C.). The results of the wear/durability are depicted in FIG. 5.

Figure 5:
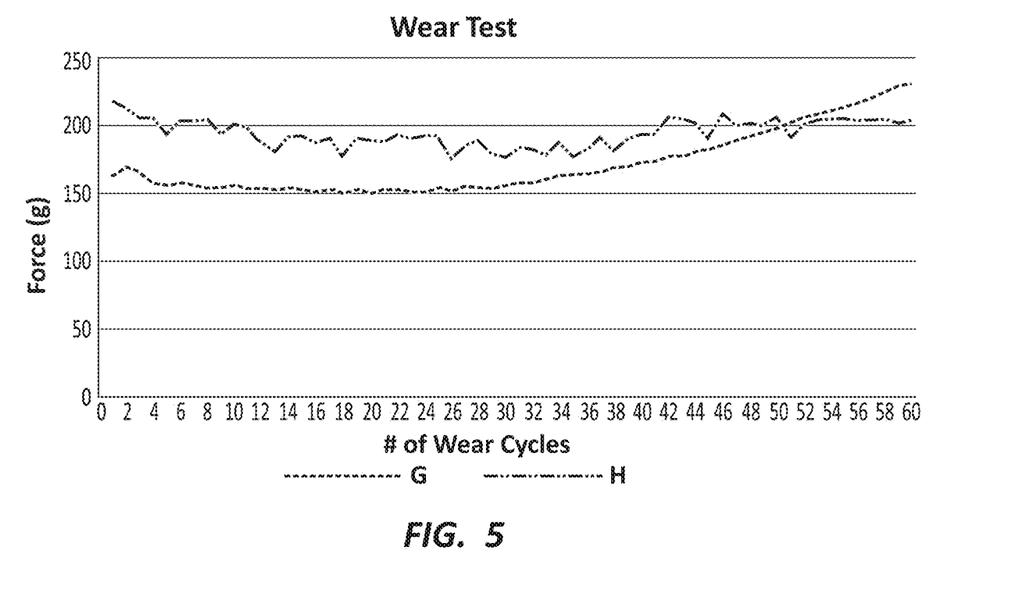
FIG. 5 is a graph of an additional wear/durability test of exemplary coatings.

As shown in FIG. 5, the wear/durability of Sample H (including PMMA having a molecular weight of 350,000 g/mol) was better than the wear/durability of Sample G (including PMMA having a molecular weight of 120,000 g/mol).

Example 4

The wear/durability of an illustrative coating (Sample I) was also compared to a comparative hydrophilic coating (Sample J) as shown in the following table (wherein the amounts are weight ratios):

| Top Coating (Sample #) | Toughening Polymer PMMA | Lubricative Polymer Poly(Methyl Vinyl Ether-co-Maleic Anhydride) (in Methyl Acetate/Methyl Ethyl Ketone) | Crosslinker (Optional) Trimethylolpropane Ethoxylate | Curing Temp. | Curing Time |
|---|---|---|---|---|---|
| I | 1 (MW 350,000 g/mol) | 100 | 0.05 | 110° C. | 16 hours |
| J | 0 | 100 | 0 | 85° C. | 2 hours |

Samples I and J were subjected to a wear/durability test using an OakRiver Technology DL1000 lubricity/wear tester. In doing so, the pads of the tester were covered with woven gauze before the wire was tested. Initially high grip force was applied and then the wire was pulled with a specific speed. The parameters of the test were as follows: test distance (100 mm); cycles (60); speed (10 mm/s); acceleration (200 mm/s) grip force (900 g); environment (PBS 1×, 37° C.). The results of the wear/durability are depicted in FIG. 6.

Figure 6:
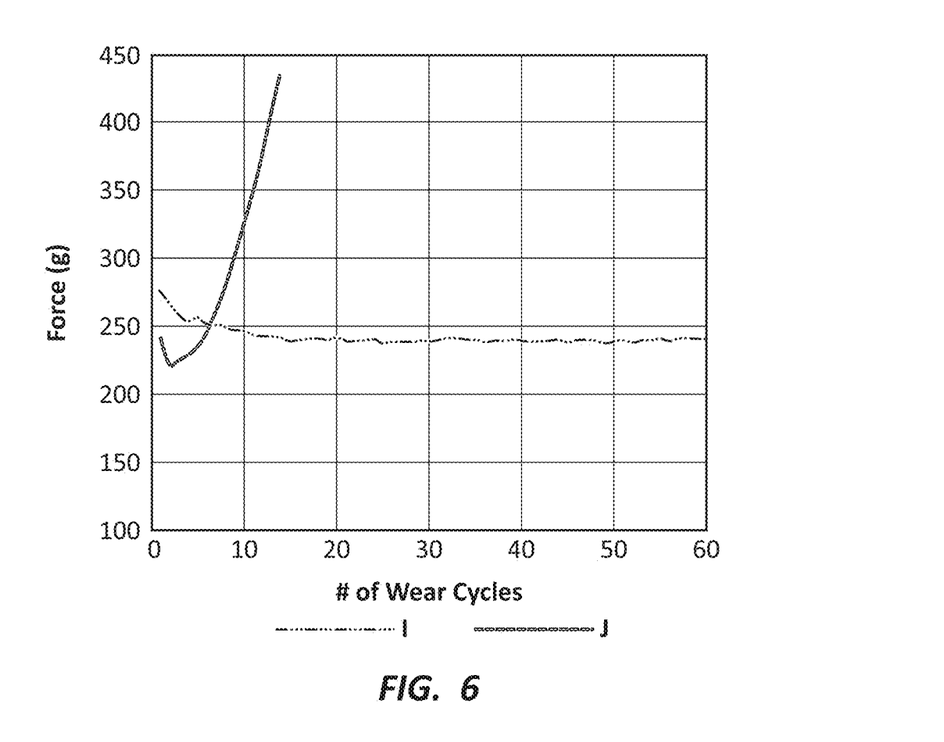
FIG. 6 is a graph of an additional wear/durability test of exemplary coatings.

As shown in FIG. 6, the wear/durability of Sample I was significantly better than the wear/durability of the comparative Sample J, as Sample J showed failure after 5-10 cycles.

References to approximations are made throughout this specification, such as by use of the term "substantially." For each such reference, it is to be understood that, in some embodiments, the value, feature, or characteristic may be specified without approximation. For example, where qualifiers such as "about" and "substantially" are used, these terms include within their scope the qualified words in the absence of their qualifiers. For example, where the term "substantially alternating" is recited with respect to a feature, it is understood that in further embodiments, the feature can have a precisely alternating configuration.

Any methods disclosed herein include one or more steps or actions for performing the described method. The method steps and/or actions may be interchanged with one another. In other words, unless a specific order of steps or actions is required for proper operation of the embodiment, the order and/or use of specific steps and/or actions may be modified. Moreover, sub-routines or only a portion of a method described herein may be a separate method within the scope of this disclosure. Stated otherwise, some methods may include only a portion of the steps described in a more detailed method.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description.

Without further elaboration, it is believed that one skilled in the art can use the preceding description to utilize the invention to its fullest extent. The claims and embodiments disclosed herein are to be construed as merely illustrative and exemplary, and not a limitation of the scope of the present disclosure in any way. It will be apparent to those having ordinary skill in the art, with the aid of the present disclosure, that changes may be made to the details of the above-described embodiments without departing from the underlying principles of the disclosure herein. In other words, various modifications and improvements of the embodiments specifically disclosed in the description above are within the scope of the appended claims. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified. The scope of the invention is therefore defined by the following claims and their equivalents.

The invention claimed is:

1. A medical device, comprising:
   a body having an exterior surface;
   a jacket coating disposed on the exterior surface;
   a base coating layer disposed on the jacket coating and comprising a polyurethane;

a top coating layer disposed on the base coating layer, said top coating layer comprising a toughening polymer comprising an acrylate polymer and a hydrophilic lubricative polymer, wherein the lubricative polymer comprises a salt monomer, wherein a weight ratio of the toughening polymer to the lubricative polymer in the top coating layer is from about 0.001:100 to about 4:100, and wherein the toughening polymer and the lubricative polymer are present within the top coating layer as a semi-interpenetrating network in which only the lubricative polymer is chemically bonded to the base coating layer.

2. The coating of claim 1, wherein the polyurethane is an aliphatic polyether-based polyurethane.

3. The coating of claim 1, wherein the acrylate polymer is a poly(methacrylate).

4. The coating of claim 1, wherein the lubricative polymer is a maleic anhydride polymer.

5. The coating of claim 4, wherein the maleic anhydride polymer is poly(methyl vinyl ether-co-maleic anhydride) in which at least a portion of maleic anhydride monomers are maleic acid salt monomers.

6. The coating of claim 1, wherein the lubricative polymer is at least partially crosslinked by a crosslinker.

7. The coating of claim 1, wherein the salt monomer is a monovalent salt.

8. The coating of claim 1, wherein the salt monomer is a divalent salt.

9. A medical device having a durable lubricious coating, comprising:
a body having an exterior surface;
a jacket coating disposed on the exterior surface;
a base coating layer disposed on the jacket coating and comprising an aliphatic polyether-based polyurethane bonded to the jacket coating;
a top coating layer disposed on the base coating layer and comprising a toughening polymer comprising an acrylate polymer and a hydrophilic lubricative polymer, wherein the lubricative polymer comprises a salt monomer, wherein a weight ratio of the toughening polymer to the lubricative polymer in the top coating layer is from about 0.001:100 to about 4:100,
wherein the toughening polymer and the lubricative polymer are present within the top coating layer as a semi-interpenetrating network in which only the lubricative polymer is chemically bonded to the base coating layer,
wherein the acrylate polymer is a poly(methacrylate), and
wherein the lubricative polymer is poly(methyl vinyl ether-co-maleic anhydride) in which at least a portion of maleic anhydride monomers are maleic acid salt monomers.

10. A method of coating a medical device having a jacket coating on an exterior surface, comprising:
forming a base coating layer comprising a polyurethane on the jacket coating;
forming a top coating layer on the base coating layer, wherein the top coating layer comprises a toughening polymer and a lubricative polymer, said lubricative polymer comprising a saltable monomer, wherein a weight ratio of the toughening polymer to the lubricative polymer in the top coating layer is from about 0.001:100 to about 4:100;
curing the top coating layer to bind the lubricative polymer to the base coating layer while leaving the toughening polymer unbound; and
activating the top coating layer to render the top coating layer hydrophilic,
wherein the toughening polymer is a poly(methacrylate), and
wherein the lubricative polymer is poly(methyl vinyl ether-co-maleic anhydride).

11. The method of claim 10, wherein the top coating layer formulation further comprises a crosslinker.

12. The method of claim 10, wherein activating the top coating layer comprises converting the saltable monomer to a salt.

13. The method of claim 12, wherein the salt is a monovalent salt.

14. The method of claim 10, wherein the saltable monomer is an acid anhydride and activating the top coating layer comprises:
converting the acid anhydride to an acid; and reacting the acid with a base.

15. The method of claim 13, further comprising finishing the top coating layer by converting the monovalent salt to a divalent salt.

* * * * *